United States Patent
Song et al.

(10) Patent No.: US 7,994,303 B2
(45) Date of Patent: Aug. 9, 2011

(54) PENAEIDIN GENE PROMOTERS IN TIGER SHRIMP AND APPLICATIONS THEREOF

(75) Inventors: Yen-Ling Song, Taipei (TW); Shih-Hu Ho, Jiaosi Township (TW)

(73) Assignee: National Taiwan University, Taipei (TW)

( * ) Notice: Subject to any disclaimer, the term of this patent is extended or adjusted under 35 U.S.C. 154(b) by 24 days.

(21) Appl. No.: 12/509,305

(22) Filed: Jul. 24, 2009

(65) Prior Publication Data

US 2010/0306865 A1      Dec. 2, 2010

(51) Int. Cl.
 *C07H 21/04* (2006.01)
 *C12N 15/00* (2006.01)
 *A01K 67/00* (2006.01)
(52) U.S. Cl. ..................... 536/24.1; 435/320.1
(58) Field of Classification Search .......................... None
 See application file for complete search history.

(56) References Cited

OTHER PUBLICATIONS

Ho et al. Cloning of penaeidin gene promoter in tiger shrimp (*Penaeus monodon*). Fish & Shellfish Immunology 27:73-77, 2009.*
O'Leary, Nuala A., et al, "*Genomic Structure and Transcriptional Regulation of the Penaeidin Gene Family from Litopenaeus Vannamei*", Science Direct, Gene 371 (2006) 75-83.
Tseng, F.S., et al., "*Introducing Foreign DNA Into Riger Shrimp (Penaeus Monodon) by Electroporation*", Theriogenology 54:1 1421-1432, 2000.

* cited by examiner

*Primary Examiner* — Quang Nguyen
(74) *Attorney, Agent, or Firm* — Volpe and Koenig, P.C.

(57) ABSTRACT

The present invention relates to new penaeidin gene promoters found in tiger shrimps and applications thereof. The promoters of the invention are useful for the development of transgenic shrimps and valuable for the shrimp culture industry.

7 Claims, 2 Drawing Sheets

(A)

```
                         ACCCCCTTTGAGAACTCTCCTGACAACGCTTACTAACAGCTTGCCTGTTGTATAGT -401
                                        AP-1                                      AP-1
GTCAGATGGTCTCCATTACGTGTGGTATATGTTTAAAAAAAAAGGGAGGTTTAAAAGTTAAAATTGATGATGATGATGGT -321
GAATAATGATGAAACTGAAAAATCTTATATTTTTTCCATGTTTTTTATCTGTCTGTCTGTTAATCTAATAGTTAGCTATC -241
AP-1    GATA-3  dorsal GATA-3          GATA                                GATA
TATCTATTTACCATTCTGTTTAGTTTTGAGTCTCTTTTTTCTATTTGTCTCTATGCCTATTTATATTTCTTTCTTTCCCTC -161
                                dorsal
TTACCCCCCTTCCCTCTCTCTCTCTCTCTCTCTCTCTCTCTCTCTCTCTCTCCTTTCTCTATCTATCTCTACCTTCCTGT -81
                                                           GATA
CTTTCTCTCCCCCCGTCTCTCTCTTTAAAACTGCTTGCACAACCGCGTGGCGTCTCTATAAAAGCACCACAGCCCCCGGT -1
                                                       TATA-box
GCCAGTCGGTGCTTGGCTCTCACCTGACCCCCACCTGTAGAGGCCGAGACTCCTTGCCCGGGTTCCTTCCTGTGTCCGCC +80
+1                       AP-1                           Xma I
ATG
ORF Start                                          +62
```

(B)

```
                                                                  CATTTACATGA -321
AATTGAAAAGAACTGGACATCGTTTGAAAACCCACTAGATTCTCCCTCTTTTCTCGTTCTCTCTGTCTGCCTTCCTGTTT -241
                              dorsal         dorsal
GTCTGTCTGTCTGTCTGTCTCTCTCTCTATATATGCTATATATGTATACATATGTATACTTCAAAGACCTTACACATCTC -161
AATATATATGCATATATATGTGTGTGTGTGTGTGTGTGTGTGTGTGTGTGTGTGTGTGTGCATGTGTGTATAGATGTA -81
                                                                       GATA-3
TGTAAAGCATGGAAAACGACTCAAGGTGCTTGCACAACATCGTGGCGTCTCTATATAAGCCAGCCACCTCAGCTTCCAGT -1
     dorsal                                          TATA-box
ACCAGTCGGTGCTTGGCTCTCACCTGACCCCCACCTGTAGAGGCCGAGACTCCTTGCCCGGGTTCCTTCCTGTGTCCGCC +80
+1                       AP-1                           Xma I
ATG
ORF Start                                          +62
```

PENAEIDIN GENE PROMOTERS IN TIGER SHRIMP AND APPLICATIONS THEREOF

CROSS-REFERENCE TO RELATED APPLICATION PARAGRAPH

This application claims the benefit of Taiwan Patent Application No. 098117710 filed on May 27, 2009, the content of which is hereby incorporated by reference in its entirety.

BACKGROUND OF THE INVENTION

The present invention relates to penaeidin gene promoters found in tiger shrimps and applications thereof.

Tiger shrimps are the most economically important shrimp species in the world. Large-scale tiger shrimp cultures exist in Southeastern Asia, South Pacific, and Middle and South America, which generated over 400,000 tons of production and over 3 billion U.S. dollars of revenue in 1997. However, the tiger shrimp culture industry in Taiwan almost collapsed in recent years because of the great loss caused by the deterioration of culture environment and the outburst of infectious diseases.

To save tiger shrimp culture industry in Taiwan, many studies aimed at the aspects of culture environment, feed, shrimp diseases, selection of specific-pathogen-free (SPF) shrimp spawners or fry, and shrimp breeding, for example. However, it is difficult to achieve the purpose of disease control by altering the culture environment, such as adjusting the temperature, salt level, pH value, and $NH_3$ level since the optimal growing conditions of pathogens usually overlap with those of shrimps. In addition, although the survival rate of shrimps can be raised by supplementing feed with glucan that increases the general disease resistance, it is limited by the narrow dose range of immunostimulants, and negative effects are resulted if high doses are used. Furthermore, although the technique for selecting SPF shrimp spawner or fry has matured, it is still costly to screen for the shrimp spawner or fry that contains no commonly known pathogens, and the number of such shrimp spawner or fry is small currently. Besides, the thus obtained SPF shrimps must be farmed in isolated space with circulating water. If they are farmed in a traditional outdoor pool where it is hard to keep these shrimps away from pathogens, their mortality rate would even exceed that of shrimps with a slight illness. As for the use of antibiotics, there exists the problem of residue although they are effective. The prices of shrimps farmed in China, Thailand, Vietnam and India have fallen greatly since the European Union published the report on antibiotic residue in farmed shrimps, seriously damaging the development of shrimp farmers industry.

Penaeidins belong to a family of antimicrobial peptides that exhibit both Gram-positive antibacterial and antifungal activities. They have been found in *Litopenaeus, Marsupenaeus, Fenneropenaeus, Penaeus* and *Farfantepenaeus* shrimps. Penaeidins are constitutively synthesized and stored in the shrimp hemocytes, located in granulocyte-cytoplasmic granules, and released in response to appropriate stimuli such as infections. Three classes of penaeidins, PEN2, PEN3 and PEN4, were identified in the Pacific white shrimp *L. vannamei*, each class being encoded by a unique gene, and among which PEN3 exhibited the highest mRNA expression. Tiger shrimp *Penaeus monodon* was found to have one class of penaeidin, high mRNA expression of which was detected during the nauplius I and intermoult stages.

There are many successful examples of introducing heterologous genes which provide desired characteristics of strong disease-resistance, high stress-endurance, and increased growth rate into fish and shellfish by genetic transformation techniques. Tseng et al. introduced heterologous DNA into tiger shrimps by electroporation to express a reporter gene (Theriogenology. 2000; 54(9):1421-32). They used an expression vector comprising a promoter derived from a mammalian virus. Although the promoter can be recognized by most biological systems, the disadvantage is leaving a virus-derived DNA fragment in the transgenic shrimp.

BRIEF SUMMARY OF THE INVENTION

In one aspect, the present invention provides an isolated nucleic acid molecule comprising a nucleotide sequence selected from the group consisting of SEQ ID NOS: 1 and 2 and fragments thereof. In one embodiment, the nucleic acid molecule of the invention comprises a nucleotide sequence of SEQ ID NO: 3. In another embodiment, the nucleic acid molecule of the invention comprises a nucleotide sequence of SEQ ID NO: 4.

In another aspect, the present invention provides a vector comprising a first nucleic acid fragment comprising a nucleotide sequence selected from the group consisting of SEQ ID NOS: 1 and 2 and fragments thereof. In one embodiment, the first nucleic acid fragment comprises a nucleotide sequence of SEQ ID NO: 3. In another embodiment, the first nucleic acid fragment comprises a nucleotide sequence of SEQ ID NO: 4. The vector of the invention may further comprise a second nucleic acid fragment which encodes a protein and is operatively linked to the first nucleic acid fragment.

In yet another aspect, the present invention provides a transgenic shrimp comprising the nucleic acid molecule as described herein.

The various embodiments of the present invention are described in details below. Other characteristics of the present invention will be clearly presented by the following detailed description about the various embodiments and claims.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings:

FIG. 1 shows the sequences, transcription factor binding sites, and restriction sites of (A) Promoter 536 (SEQ ID NO: 1) with the ATG start site and (B) Promoter 411 (SEQ ID NO: 2) with the ATG start site of the present invention. The transcription start sites are indicated as +1. The arrows represent the PCR primers. The transcription factor binding sites and restriction sites are underlined.

DETAILED DESCRIPTION OF THE INVENTION

Figure 2:
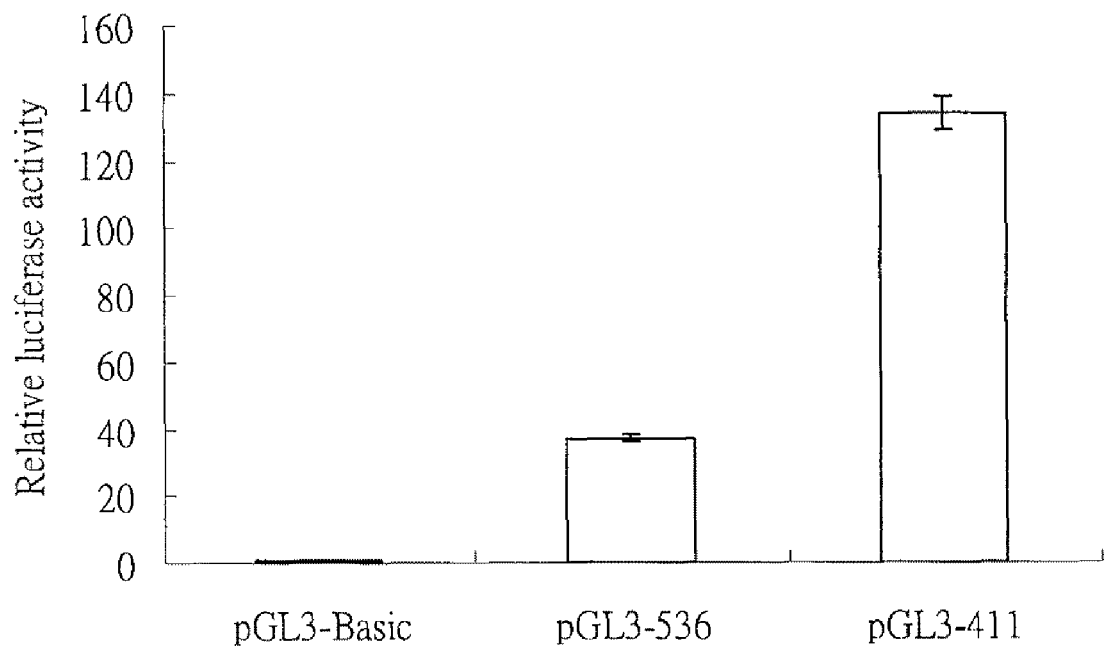
FIG. 2 shows the results of the luciferase activity assay for Promoter 536 and Promoter 411 of the present invention. The luciferase activity as detected is expressed as fold induction relative to the empty vector (pGL3-Basic). The error bars represent ±S.D. of duplicate experiments. The statistical data indicate that Promoter 536 and Promoter 411 were significantly active when compared with the empty vector (p<0.01, ANOVA/Duncan), and that Promoter 411 was significantly active when compared with Promoter 536 (p<0.01, ANOVA/Duncan).

The present invention features two novel promoter sequences, Promoter 536 and Promoter 411, identified from the upstream sequence of the penaeidin gene in tiger shrimps (*Penaeus monodon*). The promoters were found active and thus are useful in the development of transgenic shrimps and beneficial for the shrimp farming industry.

Unless defined otherwise, all technical and scientific terms used herein have the meaning commonly understood by a person skilled in the art to which this invention belongs.

The articles "a" and "an" are used herein to refer to one or more than one (i.e., at least one) of the grammatical object of the article.

In one aspect, the present invention provides an isolated nucleic acid molecule comprising a nucleotide sequence selected from the group consisting of SEQ ID NOS: 1 and 2 and fragments thereof. According to the present invention, said "fragment" refers to a fragment of SEQ ID NO: 1 or 2 with a length suitable for expressing a protein (e.g. penaeidins), such as the nucleotide sequence of SEQ ID NO: 3 or 4. That is, in one embodiment, the nucleic acid molecule of the present invention comprises a nucleotide sequence of SEQ ID NO: 3. In another embodiment, the nucleic acid molecule of the present invention comprises a nucleotide sequence of SEQ ID NO: 4. The nucleic acid molecule of the present invention is isolated from the upstream sequence of the penaeidin gene in tiger shrimps and functions as a promoter.

The term "nucleic acid", "nucleic acid molecule" or "nucleic acid fragment" refers to a polymer composed of nucleotide units, which can be single-stranded or double-stranded, linear or circular, deoxyribonucleic acid (DNA) or ribonucleic acid (RNA). A nucleotide unit comprises a base, a ribose, and a phosphate moiety. Common base moiety for nucleotides includes guanine (G), adenine (A), cytosine (C), thymine (T) and uracil (U), wherein adenine is paired with thymine or uracil, and guanine is paired with cytosine.

The term "isolated nucleic acid molecule" used herein refers to nucleic acids purified from a natural organism, or those manufactured by chemical synthesis or PCR amplification. For methods of nucleic acid purification, chemical synthesis and PCR amplification, see, for example, Molecular Cloning: A Laboratory Manual, $2^{nd}$ ed., Cold Spring Harbor Laboratory Press (Sambrook J. et al., 1989), and Current Protocols in Molecular Biology, John Wiley & Sons, Inc. (Frederick M. A. et al., 2001). A person of ordinary skill in the art can obtain the nucleic acid molecule of the present invention based on known technology in light of the teachings as disclosed herein. Detailed methods are described in the following examples.

The nucleic acid molecule of the present invention has promoter activity and may be used to express a genetic sequence operatively linked to it.

Therefore, in another aspect, the present invention provides a vector comprising a first nucleic acid fragment comprising a nucleotide sequence selected from the group consisting of SEQ ID NOS: 1 and 2 and fragments thereof. In one embodiment, the first nucleic acid fragment of the vector comprises a nucleotide sequence of SEQ ID NO: 3. In another embodiment, the first nucleic acid fragment of the vector comprises a nucleotide sequence of SEQ ID NO: 4.

Preferably, the vector of the present invention further comprises a second nucleic acid fragment which encodes a protein and is operatively linked to the first nucleic acid fragment. The term "operatively linked" or similar terms used herein refers to the way a promoter sequence is linked to another nucleotide sequence encoding a particular genetic product, by which said nucleotide sequence is controlled or regulated by the promoter to express the genetic product under suitable conditions.

The vector of the present invention may optionally comprise other sequences with specific functions, such as a replication origin, a termination sequence, and a marker gene for screening purpose (such as an anti-antibiotic gene). A person of ordinary skills in the art can select suitable sequences based on current knowledge and construct the vector of the present invention with known genetic engineering techniques. For genetic engineering techniques required for constructing a recombinant vector, such as polymerase chain reaction (PCR) amplification, nucleic acid purification, and enzymatic treatment and sequencing of vectors and nucleic acid fragments, see, for example, Molecular Cloning: A Laboratory Manual by Sambrook J. et al. and Current Protocols in Molecular Biology by Frederick M. A. et al. (supra). Specific details for vector construction are described in the following examples.

The vector of the present invention may be introduced into a host cell to amplify the nucleotide sequence carried therein or express the encoded protein.

Therefore, in yet another aspect, the present invention provides a host cell comprising the above-described vector. The host cell of the present invention may be prokaryotic (such as bacteria) or eukaryotic (such as insect cells).

Specifically speaking, the host cell of the present invention comprises a vector comprising a first nucleic acid fragment comprising a nucleotide sequence selected from the group consisting of SEQ ID NOS: 1 and 2 and fragments thereof. In one embodiment, the first nucleic acid fragment comprises a nucleotide sequence of SEQ ID NO: 3. In another embodiment, the first nucleic acid fragment comprises a nucleotide sequence of SEQ ID NO: 4. The host cell of the present invention may be used, for example, to amplify the first nucleic acid fragment.

Preferably, the vector in the host cell of the present invention further comprises a second nucleic acid fragment which encodes a protein and is operatively linked to the first nucleic acid fragment. The host cell of the present invention may be used, for example, to express the protein encoded by the second nucleic acid fragment.

There are plenty of literatures in the field describing various transformation techniques, such as calcium chloride treatment, electroporation, lipofection and microinjection. A person of ordinary skills in this art can select a suitable technique for preparing the host cell of the present invention in view of the species of the host cell and the properties of the vector to be introduced into the host cell.

In yet another aspect, the present invention provides a method of expressing proteins using the above vector. The method of the present invention comprises (1) introducing into a host cell a vector comprising a first nucleic acid fragment and a second nucleic acid fragment, wherein the first nucleic acid fragment comprises a nucleotide sequence selected from the group consisting of SEQ ID NOS: 1 and 2 and fragments thereof, and the second nucleic acid fragment encodes a protein and is operatively linked to the first nucleic acid fragment; and (2) expressing the protein encoded by the second nucleic acid fragment under suitable conditions. In an embodiment, the first nucleic acid fragment comprises a nucleotide sequence of SEQ ID NO: 3. In another embodiment, the first nucleic acid fragment comprises a nucleotide sequence of SEQ ID NO: 4.

In a further aspect, the present invention provides a transgenic shrimp comprising the nucleic acid molecule or vector as described herein.

The transgenic shrimp of the invention can be prepared based on known standard transgenic techniques in light of the teachings as provided herein. In particular, the nucleic acid molecule of the present invention may be introduced into the nucleus or cytoplasm of animal gametes, embryos or somatic cells by known methods such as injection, electrification, particle gun or chemical reagent, whereby the nucleic acid molecule of the present invention can be replicated in the embryo or cell and further expressed in the individual. As used herein, the transgenic shrimp according to the invention includes but is not limited to tiger shrimp (Penaeus monodon), pacific white shrimp (Litopenaeus vannamei), fleshy prawn (Fenneropenaeus chinensis), white shrimp (Litopenaeus setiferus), blue shrimp (Litopenaeus stylirostris), kuruma shrimp (Penaeus japonicus), and giant freshwater prawn (Macrobrachium rosenbergii).

The various embodiments of the present invention are described in details below. Other characteristics of the present invention will be clearly presented by the following detailed description about the various embodiments and claims.

Example 1

Extraction of Genomic DNA

The method of extracting tiger shrimp genomic DNA was modified from the mammalian protocol. Briefly, hemolymph from tiger shrimp (Penaeus monodon) was collected using a syringe containing anticoagulant (0.1 M sodium citrate, 0.4 M sucrose, 0.01 M Tris-HCl, pH 7.6, osmolarity adjusted to 780 mOsm/kg by adding sucrose) and centrifuged at 700×g for 15 min at 4° C. The resulting hemocyte pellet was lysed in lysis buffer (10 mM Tris-HCl, 0.1 M EDTA, 0.5% (w/v) SDS, 20 µg/mL RNase A, pH 8.0) and incubated for 1 hr at 37° C. Proteinase K (final conc. 100 µg/mL) was then added into the lysate, which was further incubated for another 3 hrs at 50° C. The lysate was purified by phenol:chloroform:isoamyl alcohol (25:24:1, Amresco) extraction. Aqueous phases were pooled and DNA was precipitated by adding 0.2 volume of 10 M ammonium acetate and 2 volume of ethanol. After washing with 70% ethanol, DNA was dried and dissolved in a solution containing 10 mM Tris-HCl and 1 mM EDTA, pH 8.0.

Example 2

Extender and Nested Polymerase Chain Reaction (PCR)

The cloning of penaeidin gene upstream sequence was modified from the extender polymerase chain reaction method. Briefly, genomic DNA was partially digested with RsaI. Digested DNA was ethanol-precipitated, washed, dried, dissolved and then ligated with adapters which were prepared by annealing two oligonucleotides, 5'-TGCGAGTAAG-GATCCTCACGCAAGGAATTCCGACCAGA-CACCCTAG-3' (SEQ ID NO: 5) and 5'-/5Phos/-CTAGGGT-GTCTGGTCGC-3' (SEQ ID NO: 6). Unligated adapters were removed by Sephadex G-200 or Montage™ PCR Centrifugal Filter Devices (Millipore).

Using the ligated DNA as template, a first round PCR (25 cycles of 1 min at 94° C., 30 sec at 64° C. and 1 min 30 sec at 72° C.) was run using 1 pmole forward adapter P1 primer 5'-TGCGAGTAAGGATCCTCACGCA-3' (SEQ ID NO: 7) and 10 pmole reverse penaeidin specific primer 5'-CAG-GAAGACCAGGCAGACCACGAGA-3' (SEQ ID NO: 8; designed according to the penaeidin cDNA sequence of GenBank Accession No. AF475082).

The product of the first round PCR was subjected to a nested second round PCR (1 min at 94° C. followed by 30 cycles of 20 sec at 94° C., 20 sec at 66° C. and 1 min at 72° C.) using 10 pmole adapter P2 primer 5'-CGCAAGGAATTC-CGACCAGACA-3' (SEQ ID NO: 9) and 10 pmole reverse penaeidin specific primer 5'-CCATGGCGGACACAG-GAAGGAACCC -3' (SEQ ID NO: 10). The product was subjected to electrophoresis, and the band on the electrophoresis gel was cut out and eluted. The thus obtained DNA was ligated to the pGEM-T Easy vector (Promega). The ligated vector was subsequently introduced into E. coli DH-5α competent cells to amplify the vector.

Clones were sent to a commercial company, Mission Biotech, Taiwan, for sequencing. A sequence of 536 bp (SEQ ID NO: 1; GenBank Accession No. FJ418753) was obtained and designated as "Promoter 536" (FIG. 1A).

Example 3

Extender and Nested PCR

Based on the method of Example 2, primers designed from the more upstream sequence of penaeidin gene were used for extender and nested PCR. Briefly, the first round PCR was run using genomic DNA as template and the forward primer 5'-CATTTAAATTAGTTAATGGCTTCTGC-3' (SEQ ID NO: 11) and reverse primer 5'-ACTATCACCTGATTAATA-CATGACCTT-3' (SEQ ID NO: 12; designed from the penaeidin gene intron of GenBank Accession No. FJ227936).

The product of the first round PCR was subjected to the nested second round PCR using the forward primer 5'-CATT-TACATGAAATTGAAAAGAACTG-3' (SEQ ID NO: 13) and reverse penaeidin intron primer 5'-TTGGTAAGACAG-TAGACTCATGGTT-3' (SEQ ID NO: 14). The obtained PCR product was cloned into the pGEM-T Easy vector and sequenced. A sequence of 411 bp (SEQ ID NO: 2; GenBank Accession No. FJ418752) was obtained and designated as "Promoter 411" (FIG. 1B).

Example 4

Analysis of Promoter Sequence Structure

The transcription start sites of Promoter 536 and Promoter 411 were identified based on the previous cDNA sequence (GenBank Accession No. AF475082) and found consistently at 80 bp upstream of ATG.

In addition, the sequences were analyzed for potential transcription factor binding sites with the Match™-1.0 Public/TRANSFAC® 6.0 program (Biobase, Wolfenbüttel, Germany) using high quality matrices and 0.85 as matrix and core similarity cut-off. Accordingly, TATA box motifs were identified in position 17-31 bp ahead of transcription start sites in the sequences of Promoter 536 and Promoter 411. Other motifs, GATA, dorsal and AP-1, were found in Promoter 536 and Promoter 411 as well; however, neither STAT nor zinc-finger motifs were identified in these two promoters.

Comparatively, as taught in the prior art, in Pacific white shrimps (Litopenaeus vannamei), STATx, AP-1, dorsal and GATA motifs, involved in the transcriptional regulation of immune-gene in other arthropods, were found in the PEN4 promoter (619 bp); in the PEN 2 promoter (278 bp), only GATA and zinc-finger motifs were found; and in the PEN3 promoter (148 bp), only zinc-finger motifs were found. Additionally, AP-1 and GATA motifs were found in the upstream region of another antimicrobial peptide anti-lipopolysaccharide factor of *P. monodon*.

Example 5

Construction and Transfection of Luciferase Plasmids as Well as Promoter Activity Assays Thereof Truncated fragments of Promoter 536 and Promoter 411, from the 5'-end to +62 bp (SEQ ID NOs: 3 and 4, respectively), were respectively subcloned into the *SacI/XmaI* site of the pGL3-Basic firefly luciferase reporter vector (Promega). These two plasmids were named pGL3-536 and pGL3-411, respectively. *Drosophila* S2 cells were selected to be used for testing shrimp promoter activity. The cells were routinely cultured in Schneider's *Drosophila* Medium (Invitrogen) supplemented with 10% fetal calf serum (FCS) and grown at 26° C.

The luciferase assay was performed using the Dual-Glo luciferase assay system (Promega) with the *Renilla* luciferase gene vector as an internal control for normalization of transfection efficiency. Transfection experiments were performed in 24-well cell culture plates. Briefly, recipient S2 cells were seeded at a density of 80-90% confluence. After removal of culture medium and single wash using fresh medium without FCS, the cells were cotransfected with 1 µg firefly luciferase reporter construct DNA and 0.1 µg control plasmid (*Renilla* luciferase gene) per well using 2 µL Cellfectin Transfection Reagent (Invitrogen) in 200 µL medium without FCS according to the manufacturer's recommendations. At 20 hrs post transfection, 200 µL medium with 20% FCS was added. Cells were harvested at 28 hrs post transfection; firefly and *Renilla* luciferase activity was measured by the Dual-Glo luciferase assay system according to the manufacturer's instructions; and chemiluminescence was read by a Luoroskan Ascent FL reader (Labsystems). The results of the promoter activity assays were shown in FIG. 2.

As shown in FIG. 2, Promoter 536 and Promoter 411 respectively generated 37-fold and 134-fold increase in luciferase expression relative to the promoter-less vector (pGL3-Basic). These two promoters were demonstrated to have substantial promoter activity. In addition, the activity of Promoter 411 was significantly higher (3.6-fold) than that of Promoter 536.

Comparatively, as indicated in the prior art, in Pacific white shrimps, the mRNA expression of PEN3 was more abundant in unstimulated hemocytes than that of other two classes of penaeidin, as shown in the Northern blot analysis and quantitative RT-PCR; such results, however, could not be confirmed by the promoter activity of the PEN3 upstream sequence due to its short length of 148 bp (O'Leary N A, Gross P S. Genomic structure and transcriptional regulation of the penaeidin gene family from *Litopenaeus vannamei*. Gene 2006;371(1):75-83).

In addition, phylogenetic and molecular evolutionary analyses were conducted using MEGA version 4. The results showed that Promoter 536 was clustered with the promoter of *L. vannamei* PEN4, while Promoter 411 was clustered with the promoter of *L. vannamei* PEN2-1 and that of PEN3-1. Accordingly, the finding according to the present invention that Promoter 411 exhibits higher activity sounds consistent with the higher expression of PEN3 mRNA as mentioned above.

Given the above, the tiger shrimp-derived promoters of the present invention have been proved herein to be active, and have the potential to replace the virus-derived promoters in current use. In addition, as reported in the prior art, penaeidins of tiger shrimps exhibit antibacterial activities and tissue-specific expression in hemocytes; once a tiger shrimp is injured or infected, its hemocytes migrate to and gather at the injured or infected area. Accordingly, by using a hemocyte-specific promoter to generate a disease-resistant transgenic shrimp, it is possible to have the anti-pathogen effect restricted at the infected spots and thus reduce non-specific damage to the host.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

We claim:

1. An isolated nucleic acid molecule comprising the nucleotide sequence of SEQ ID NO: 2 or SEQ ID NO: 4.

2. A vector comprising a first nucleic acid fragment comprising the nucleotide sequence of SEQ ID NO: 2 or SEQ ID NO: 4.

3. The vector of claim 2, further comprising a second nucleic acid fragment which encodes a protein and is operatively linked to the first nucleic acid fragment.

4. The nucleic acid molecule of claim 1, comprising the nucleotide sequence of SEQ ID NO: 2.

5. The nucleic acid molecule of claim 1, comprising the nucleotide sequence of SEQ ID NO: 4.

6. The vector of claim 2, wherein the first nucleic acid fragment comprises the nucleotide sequence of SEQ ID NO: 2.

7. The vector of claim 2, wherein the first nucleic acid fragment comprises the nucleotide sequence of SEQ ID NO: 4.

* * * * *

SEQUENCE LISTING

<160> NUMBER OF SEQ ID NOS: 14

<210> SEQ ID NO 1
<211> LENGTH: 536
<212> TYPE: DNA
<213> ORGANISM: Penaeus monodon
<220> FEATURE:
<221> NAME/KEY: promoter 536
<222> LOCATION: (1)..(536)

<400> SEQUENCE: 1

```
accccctttg agaactctcc tgacaacgct tactaacagc ttgcctgttg tatagtgtca       60
gatggtctcc attacgtgtg gtatatgttt aaaaaaaaag ggaggtttaa aagttaaaat      120
tgatgatgat gatggtgaat aatgatgaaa ctgaaaaatc ttatattttt tccatgtttt      180
ttatctgtct gtctgttaat ctaatagtta gctatctatc tatttaccat tctgtttagt      240
```

-continued

```
tttgagtctc tttttctatt tgtctctatg cctatttata tttctttctt tccctcttac    300 ccccccttccc tctctctctc tctctctctc tctctctctc tctctctcct ttctctatct    360
atctctacct tcctgtcttt ctctccccccc gtctctctct ttaaaactgc ttgcacaacc    420
gcgtggcgtc tctataaaag caccacagcc cccggtgcca gtcggtgctt ggctctcacc    480 tgaccccccac ctgtagaggc cgagactcct tgcccgggtt ccttcctgtg tccgcc       536
```

<210> SEQ ID NO 2
<211> LENGTH: 411
<212> TYPE: DNA
<213> ORGANISM: Penaeus monodon
<220> FEATURE:
<221> NAME/KEY: promoter 411
<222> LOCATION: (1)..(411)

<400> SEQUENCE: 2

```
catttacatg aaattgaaaa gaactggaca tcgtttgaaa acccactaga ttctccctct     60
tttctcgttc tctctgtctg ccttcctgtt tgtctgtctg tctgtctgtc tctctctcta    120
tatatgctat atatgtatac atatgtatac ttcaaagacc ttacacatct caatatatat   180
gcatatatat gtgtgtgtgt gtgtgtgtgt gtgtgtgtgt gtgtgtgtgt gtgcatgtgt   240
gtatagatgt atgtaaagca tggaaaacga ctcaaggtgc ttgcacaaca tcgtggcgtc    300
tctatataag ccagccacct cagcttccag taccagtcgg tgcttggctc tcacctgacc    360
cccacctgta gaggccgaga ctccttgccc gggttccttc ctgtgtccgc c              411
```

<210> SEQ ID NO 3
<211> LENGTH: 518
<212> TYPE: DNA
<213> ORGANISM: Penaeus monodon
<220> FEATURE:
<221> NAME/KEY: promoter 536 (truncated)
<222> LOCATION: (1)..(518)

<400> SEQUENCE: 3

```
acccccttg agaactctcc tgacaacgct tactaacagc ttgcctgttg tatagtgtca     60
gatggtctcc attacgtgtg gtatatgttt aaaaaaaaag ggaggtttaa aagttaaaat   120
tgatgatgat gatggtgaat aatgatgaaa ctgaaaaatc ttatattttt tccatgtttt    180
ttatctgtct gtctgttaat ctaatagtta gctatctatc tatttaccat tctgtttagt   240
tttgagtctc tttttctatt tgtctctatg cctatttata tttctttctt tccctcttac    300 ccccccttccc tctctctctc tctctctctc tctctctctc tctctctcct ttctctatct    360
atctctacct tcctgtcttt ctctccccccc gtctctctct ttaaaactgc ttgcacaacc    420
gcgtggcgtc tctataaaag caccacagcc cccggtgcca gtcggtgctt ggctctcacc    480 tgaccccccac ctgtagaggc cgagactcct tgcccggg                             518
```

<210> SEQ ID NO 4
<211> LENGTH: 393
<212> TYPE: DNA
<213> ORGANISM: Penaeus monodon
<220> FEATURE:
<221> NAME/KEY: promoter 411 (truncated)
<222> LOCATION: (1)..(393)

<400> SEQUENCE: 4

```
catttacatg aaattgaaaa gaactggaca tcgtttgaaa acccactaga ttctccctct     60
tttctcgttc tctctgtctg ccttcctgtt tgtctgtctg tctgtctgtc tctctctcta    120
tatatgctat atatgtatac atatgtatac ttcaaagacc ttacacatct caatatatat   180
```

```
gcatatatat gtgtgtgtgt gtgtgtgtgt gtgtgtgtgt gtgcatgtgt        240
gtatagatgt atgtaaagca tggaaaacga ctcaaggtgc ttgcacaaca tcgtggcgtc  300
tctatataag ccagccacct cagcttccag taccagtcgg tgcttggctc tcacctgacc  360
cccacctgta gaggccgaga ctccttgccc ggg                              393
```

<210> SEQ ID NO 5
<211> LENGTH: 46
<212> TYPE: DNA
<213> ORGANISM: Artificial Sequence
<220> FEATURE:
<223> OTHER INFORMATION: adapter fragment for extender PCR

<400> SEQUENCE: 5

```
tgcgagtaag gatcctcacg caaggaattc cgaccagaca ccctag            46
```

<210> SEQ ID NO 6
<211> LENGTH: 17
<212> TYPE: DNA
<213> ORGANISM: Artificial Sequence
<220> FEATURE:
<223> OTHER INFORMATION: adapter fragment for extender PCR

<400> SEQUENCE: 6

```
ctagggtgtc tggtcgc                                            17
```

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7

```
tgcgagtaag gatcctcacg ca                                      22
```

<210> SEQ ID NO 8
<211> LENGTH: 25
<212> TYPE: DNA
<213> ORGANISM: Artificial Sequence
<220> FEATURE:
<223> OTHER INFORMATION: PCR primer

<400> SEQUENCE: 8

```
caggaagacc aggcagacca cgaga                                   25
```

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9

```
cgcaaggaat tccgaccaga ca                                      22
```

<210> SEQ ID NO 10
<211> LENGTH: 25
<212> TYPE: DNA
<213> ORGANISM: Artificial Sequence
<220> FEATURE:
<223> OTHER INFORMATION: PCR primer

<400> SEQUENCE: 10

```
ccatggcgga cacaggaagg aaccc                                   25
```

```
<210> SEQ ID NO 11
<211> LENGTH: 26
<212> TYPE: DNA
<213> ORGANISM: Artificial Sequence
<220> FEATURE:
<223> OTHER INFORMATION: PCR primer

<400> SEQUENCE: 11
catttaaatt agttaatggc ttctgc                                            26

<210> SEQ ID NO 12
<211> LENGTH: 27
<212> TYPE: DNA
<213> ORGANISM: Artificial Sequence
<220> FEATURE:
<223> OTHER INFORMATION: PCR primer

<400> SEQUENCE: 12
actatcacct gattaataca tgacctt                                           27

<210> SEQ ID NO 13
<211> LENGTH: 26
<212> TYPE: DNA
<213> ORGANISM: Artificial Sequence
<220> FEATURE:
<223> OTHER INFORMATION: PCR primer

<400> SEQUENCE: 13
catttacatg aaattgaaaa gaactg                                            26

<210> SEQ ID NO 14
<211> LENGTH: 25
<212> TYPE: DNA
<213> ORGANISM: Artificial Sequence
<220> FEATURE:
<223> OTHER INFORMATION: PCR primer

<400> SEQUENCE: 14
ttggtaagac agtagactca tggtt                                             25
```